(12) United States Patent
Silva

(10) Patent No.: US 8,263,528 B2
(45) Date of Patent: Sep. 11, 2012

(54) NATURAL FLOWER PRESERVING PROCESS

(75) Inventor: Gloria Silva, Bogota (CO)

(73) Assignee: Guirnaldas S.A., Bogata (CO)

( * ) Notice: Subject to any disclaimer, the term of this patent is extended or adjusted under 35 U.S.C. 154(b) by 918 days.

(21) Appl. No.: 10/551,635

(22) PCT Filed: Apr. 1, 2004

(86) PCT No.: PCT/IB2004/000998
§ 371 (c)(1),
(2), (4) Date: Sep. 30, 2005

(87) PCT Pub. No.: WO2004/086864
PCT Pub. Date: Oct. 14, 2004

(65) Prior Publication Data
US 2007/0089363 A1     Apr. 26, 2007

(30) Foreign Application Priority Data
Apr. 2, 2003   (CO) .................................. 03027746

(51) Int. Cl.
*A01N 3/02* (2006.01)
(52) U.S. Cl. ...................................... 504/114; 504/115
(58) Field of Classification Search .................. 504/114, 504/115
See application file for complete search history.

(56) References Cited

U.S. PATENT DOCUMENTS

| 4,828,890 A | | 5/1989 | Tiedeman | |
| 5,252,537 A | * | 10/1993 | De Winter-Scailteur | 504/114 |
| 5,677,019 A | * | 10/1997 | Carstairs et al. | 428/22 |

FOREIGN PATENT DOCUMENTS

| EP | 1290940 | 3/2003 |
| ES | 2123963 | 1/1999 |
| FR | 2751510 | 1/1998 |
| WO | 9103160 | 3/1991 |
| WO | WO 03084324 | 10/2003 |

OTHER PUBLICATIONS

"A Guide to Glycols", The Dow Chemical Company, 2003.

* cited by examiner

*Primary Examiner* — Alton Pryor
(74) *Attorney, Agent, or Firm* — Baker & McKenzie LLP

(57) ABSTRACT

The present invention relates to a method for providing flowers characterized in that they have the look and feel of fresh flowers. The method comprises a selection and cutting step, a step of setting up holder devices on grids, and three optionally repeatable dehydration, infiltration and evaporation steps. The present invention does not require the use of molecular sieves during the method. The method is also technically advanced and can therefore be implemented on an industrial scale.

25 Claims, 3 Drawing Sheets

NATURAL FLOWER PRESERVING PROCESS

CROSS-REFERENCE TO RELATED APPLICATIONS

This application claims priority to PCT Application No. PCT/IB2004/0009998 filed on Apr. 1, 2004, which claims priority to Colombia Patent Application No. 03027746 filed on Apr. 2, 2003, incorporated herein by reference.

TECHNICAL SECTOR

The present invention relates with a process for obtaining flowers having the appearance and texture like fresh flowers. The flowers obtained using the process of the present invention last longer as they are not impaired by microorganisms since water contained in cells has been replaced by other substance(s) thus inhibiting microorganism growth.

INVENTION BACKGROUND

Several different methods are presently known to preserve flowers for a long time period, such as those claimed in U.S. Pat. No. 5,252,537 of Oct. 12, 1993, titled "Long-lasting cut flowers and treatment method to obtain them", filed in the name of Sari Compagnie Du Nord, Inventor Nadine De Winter-Scailteur.

Such U.S. patent divulges a method consisting of replacing the water in the flower tissue by substances inhibiting microorganisms growth. The treatment comprises a dehydration step in which water is drawn out by using an anhydrous solvent, and then is progressively absorbed into the pores of a molecular sieve. Next the solvent is replaced by a mixture of polyethylene glycol, colorants, and the same solvent used in the first step. Finally, the flowers are drained and dried. This procedure gives rise to a product failing to show smoothness and durability required by market users. Additionally, anhydrous solvents used by said method are toxic, thus causing a highly negative environment impact.

SUMMARY OF INVENTION

This invention involves the steps below:
a) Selecting and cutting (1);
b) Assembling of the supporting devices and grids (2);
c) First Dehydration (3a);
d) Second Dehydration (3b);
e) Third Dehydration (3c);
f) Optionally repeating consecutive steps of dehydration (3c)
g) Infiltration (4); and
h) Evaporation (5).
a) Selecting and Cutting (1)

This step comprises selecting flowers which are in the proper opening stage and hydrating them to ensure a turgid opening. This opening stage will last between 6 to 72 h, depending on the type of flower and its maturity stage when the cut is made.

Once the flowers have reached its optimal opening level, they are separated from the stems by cutting at a distance from and depending on the flower itself.
b) Assembling of the supporting devices and grids (2)

Figure 1:
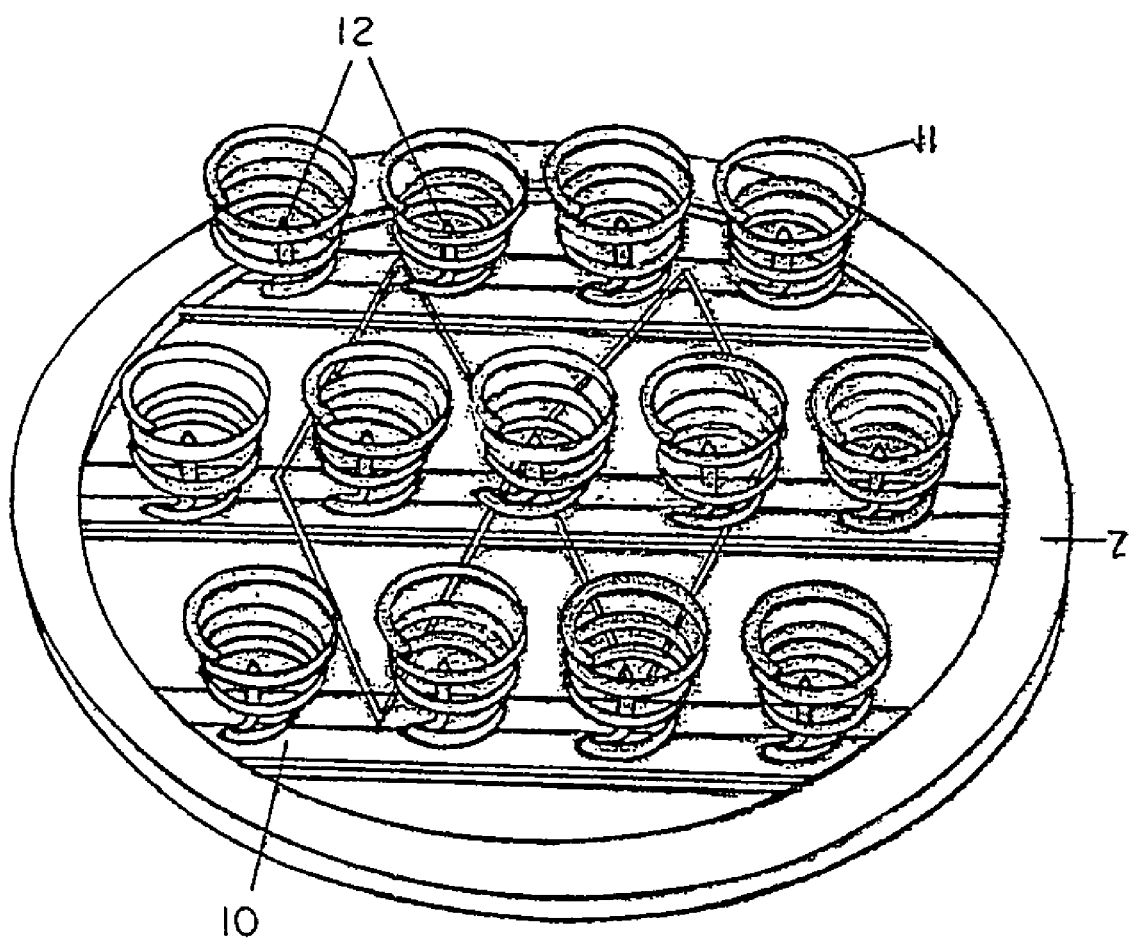
Figure 2:
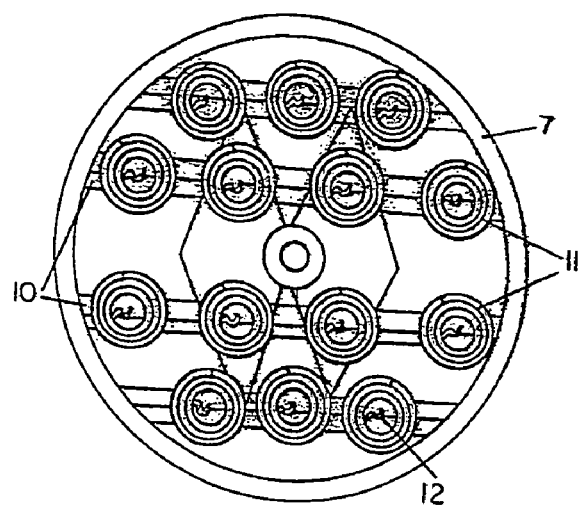

The flowers are spiked in the sharpen tips (12) of the grid's (7) spirals (11) and such grids are assembled in the central axle (9) of the supporting device (8), as shown in FIGS. 1 and 2.

The grids (7) are assembled on the central axle (9) of the supporting device (8), one on top of the previous one, with separators (13) in between, with enough distance apart so that flowers are not crushed, and which size depends on the height required for each type of flower to be processed.
c) First Dehydration (3a)

The supporting device (8) is introduced into the reactor (14). The reactor (14) is filled out until the solvent completely covers the flowers and is held at a temperature ranging between room temperature and 100° C., for at least 30 min. Then, the solvent is drawn out from the reactor (14) and recovered.
d) Second Dehydration (3b)

An ethanol-water mixture is poured into the reactor (14) having no less than 80% alcohol, previously heated at 65° C. The reactor (14) is filled out until the solvent completely covers the flowers and is maintained at a temperature no less than 65° C. for at least 30 min. Then, the solvent is drawn out from the reactor (14) and next, it is recovered.
e) Third Dehydration (3c)

A solvent comprising ethanol with an alcohol content of no less than 90%, preheated at least at 65° C. is introduced into the reactor (14). The reactor (14) is filled out until the solvent has completely covered the flowers and then is maintained at a temperature no less than 65° C. for at least 30 min. Next, the solvent is drawn out from the reactor (14).
f) Optionally, step (3c) may be successively be repeated but increasing alcohol content of the solvent in each step.
g) Infiltration (4)

The flowers are introduced and completely immersed into a bath comprised of a polyethylene glycol, ethanol and colorants mixture. The reactor is then pressurized and heated until reaching a temperature between 65° C. ant 100° C. After some treatment time, the mixture is transferred to a storing tank.
h) Evaporation (5)

The reactor (14) is subjected to vacuum between 50 kPa and 68 kPa during around 60 min. Then, the vacuum is interrupted, the reactor (14) is opened, and the supporting device 8 and grids 7 are taken out along with the flowers.

The flowers may be subjected, within the reactor, to a drying process with a hot air stream in order to completely evaporate the solvent.

The process of the present invention has several advantages compared to the current nearest state-of-the-art, U.S. Pat. No. 5,2522,357. The process of this invention is faster than the process described in the document U.S. Pat. No. 5,252,537, requiring between 6 and 18 h for the flower to be dried. The present invention uses as a dehydrating means ethyl alcohol, which is far less toxic than the solvents used in the state of the art methods. The present invention recovers, through the use of traditional methods and means, the used solvent up to a purity level that allows it to be re-utilized. The present invention does not require the use of molecular sieves during the process. The flowers obtained by the process of the present invention show a smoother texture than those obtained using the nearest state-of-the-art process. Finally, the process of the present invention is more technically advanced, allowing working at an industrial scale.

LIST OF ENCLOSED FIGURES

Figure 3:
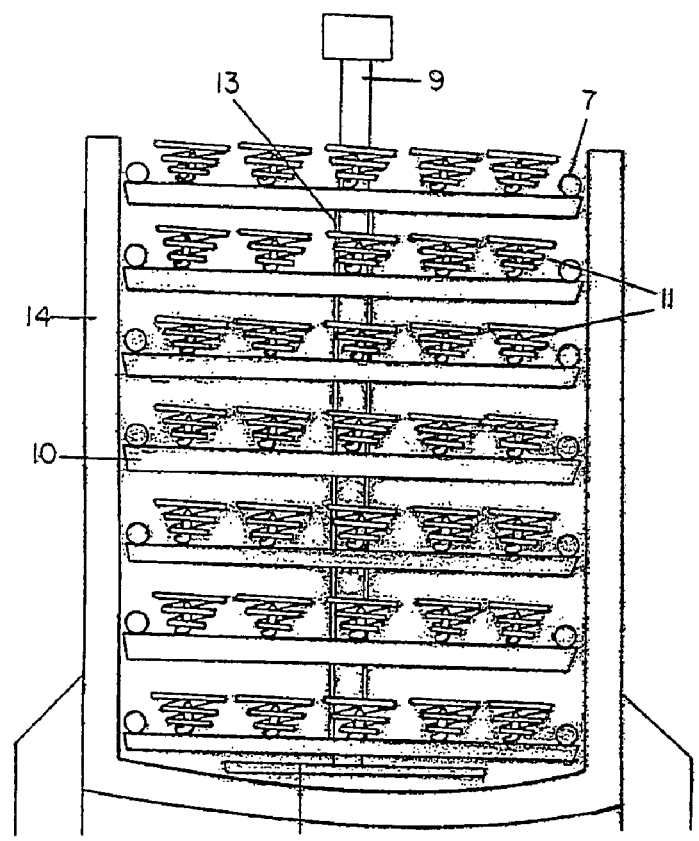
Figure 4:
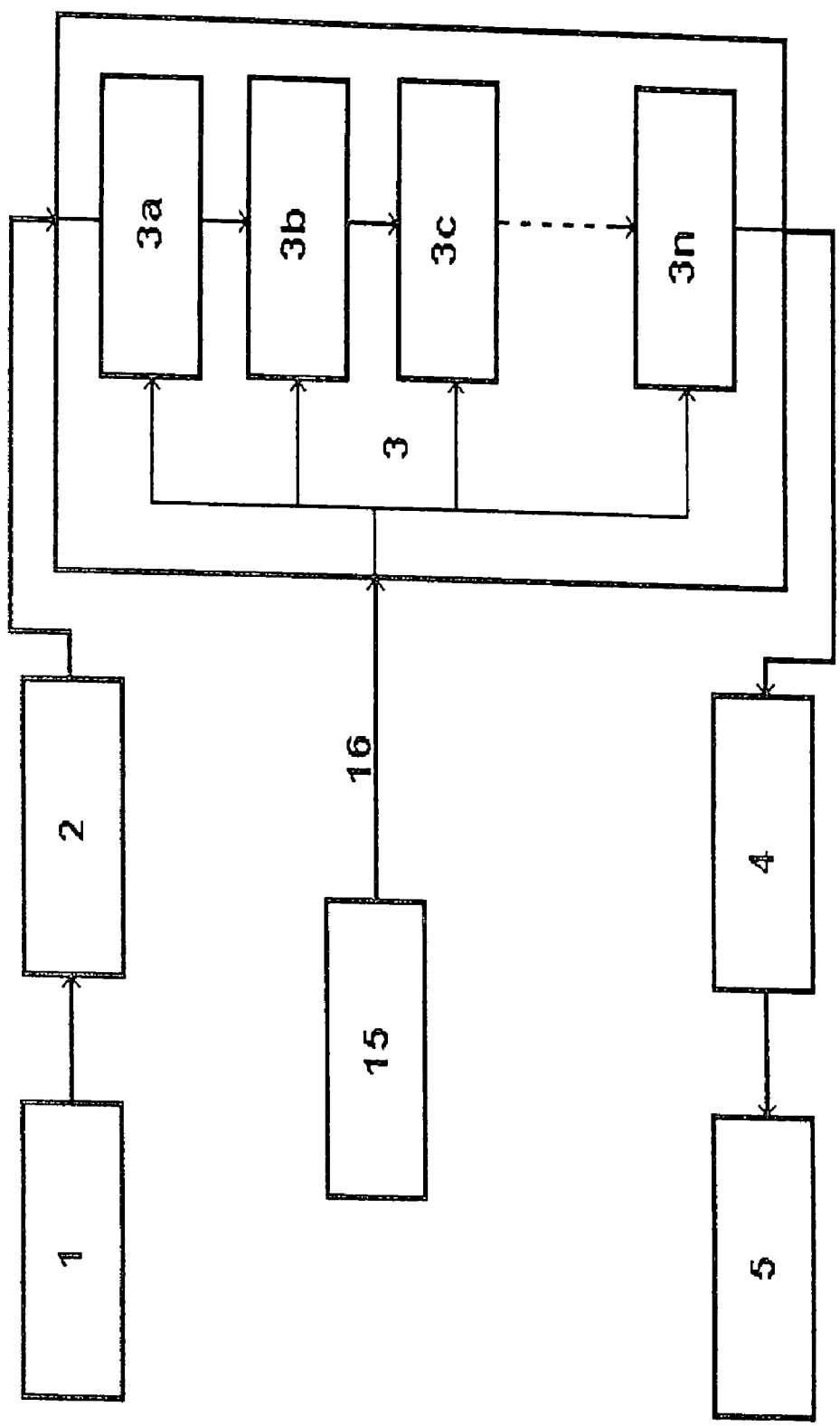

FIG. 1 shows a perspective view of the grid (7),
FIG. 2 is a top view of grid (7) of FIG. 1,
FIG. 3 is a cross-section view of the supporting device (9) and grids (7), and FIG. 4 is a block diagram of the process for preserving flowers according to the invention.

DESCRIPTION OF THE INVENTION

The present invention comprises a process for obtaining long-lasting flowers having an appearance and texture of a fresh live flower. The process of this invention is characterized by the following steps:
a) Selecting and Cutting (1);
b) Assembling of the supporting devices and grids (2);
c) First Dehydration (3a);
d) Second Dehydration (3b);
e) Third Dehydration (3c);
f) Optionally, repeating successive steps of dehydration (3c)
g) Infiltration (4);
h) Evaporation (5).

The above-mentioned steps are described below:

a) Selecting and Cutting (1)

This step consists in selecting the flowers which are already in its proper opening stage; the stems are immersed into water, so as to let them obtain a hydration level that guaranties a turgid appearance and an opening degree that shows the flower in its most attractive form, without the risk of having the petals be detached due to an excessive opening of the flower.

It must be taken into account that the opening period of the flower must be as short as possible in order to avoid losses due to fungus attack, petal falling and in general, impairment of the flower appearance. Also, a careful handling of the flowers in all the previous steps is highly desirable in order to guarantee the preservation of all petals throughout the process and thus result in a splendid flower.

This opening stage can last between 6 and 72 h, depending on the type of flower and its maturity when the cutting is made.

Once the flowers have reached its optimal opening, the stems are cut away at a distance that depends on the type of flower being processed. For example, in the of roses and carnations, the distance for the cut will range between 1 cm and 2 cm; when dealing with hydrangea, distance will vary between 10 cm and 15 cm. The flowers may or not be fixed to a device to continue with the process.

b) Assembling of the supporting devices and grids (2);

The flowers are fixed on the sharp tips (12) of the spirals (11) of the grids (7), and said grids are assembled in the central axle (9) of the supporting device (8) as shown in FIGS. 1 and 2.

The supporting device (8) comprises the grids (7), the base of which comprises channels (10) that allow for draining off liquid to the outside part of the grids (7). On such a metal channels (10), inverted frustoconical stainless steel spirals (11) have been welded, resembling the shape of the flower and which in its bottom base the wire has been perpendicularly bent and ends up in a sharp tip (12) wherein the flower stem is fixed on.

In a preferred embodiment, the grids (7) have a circular shape.

In further preferred embodiment, the grids (7) have a diameter of 64 cm.

In a preferred embodiment, the spirals (11) are made of stainless steel.

The spirals (11) allow the sepals of the flower to be in an upward position, attached to the petals, which help them to be held in position and preventing from detachment during process.

The circular grids (7) are assembled in the central axle (9) of the supporting device (8), one on top of the previous one, with tubular separators (13) placed in between enough distance apart so that the flowers are not crushed and which dimension depends on the height required for each type of flower being processed. In a preferred embodiment addressed to roses, each grid (7) has a capacity to accept 90 to 110 flowers.

The supporting device (8) accepts 1 or more grids (7) in it. In a preferred embodiment, the supporting device (8) accepts from 10 to 12 grids (7).

c) First Dehydration (3a);

The supporting device (8), once filled out with flowers, is placed into the reactor (14). In a preferred embodiment, the supporting device (8) is hung in a rail of an elevated conveyor device that permits to place it on top and then lower it down inside a reactor (14) where dehydration will be carried out.

In a preferred embodiment, the cylindrical reactor is made out of stainless steel, and can be operated up to 138 kPa pressure, or empty up to 77 kPa and at temperatures up to 200° C.

A mixture (16) of any solvent miscible in water, and water with a solvent content no less than 70% and temperature between room temperature and 100° C. is passed from a feeder tank (15), and for such a purpose, pressurized air is introduced into the feeder tank (15) and valves communicating the tank (15) with the reactor (14) are opened. The reactor (14) is filled out until solvent has completely covered the flowers maintaining the temperature ranging between room temperature and 100° C., during at least 30 min. After such time, the solvent, which has already extracted part of the water contained in the flowers, is removed from the reactor (14) and passed on another tank for its subsequent recovery through well known methods, such as distillation.

d) Second Dehydration (3b)

Upon the completion of the first dehydration stage, a mixture of any solvent miscible in water and water with a content of solvent no less than 80% and at temperature between room and 100° C. is introduced into the reactor (14). In a preferred embodiment the temperature is held at 65° C. The reactor (14) is filled out until the solvent has completely covered the flowers and is maintained at a temperature room and 100° C., for at least 30 min. In a preferred embodiment, the temperature is held at 65° C. After such time, the solvent that has extracted other portion of water contained in the flowers is withdrawn out from reactor (14) and passed on to another tank for its subsequent use or recovery through well known methods, such as distillation.

e) Third Dehydration (3c)

After the second dehydration step, a mixture of any solvent miscible in water and water with a solvent content no less than 90% and a temperature between room and 100° C. is introduced into the reactor (14). In a preferred embodiment the temperature is held at 65° C. The reactor (14) is filled out until the solvent has completely covered the flowers and is then maintained at a temperature between room and 100° C. for at least 30 min. After this time, virtually all of the water initially contained in the flowers has been replaced by an alcoholic solvent, with dehydration causing no change in the flowers shape, as its structure remains intact. The solvent is then withdrawn from the reactor ((14) and stored in another tank for a future use.

f) Optionally, step (3c) may be repeated successively but with a solvent content increase in each additional step.

The solvent used in the dehydration steps is preferably an alcohol, and even more preferably, ethanol.

g) Infiltration (4)

Upon the completion of the third dehydration step (3c), the flowers are introduced and immersed into a bath consisting of a mixture of colorants, solvent and a soluble polymer. Preferably, the polymer is polyethylene glycol, and even more preferably is polyethylene glycol 400. The reactor is heated until reaching a temperature between room and 100° C., preferably 65° C. After some time of treatment ranging between 2 and 72 h, all the solvent initially filling flower tissue, has been replaced by the mixture containing polyethylene glycol and colorants. Then, such mixture is transferred to a storing tank.

The polymer percentage in the mixture is determined according to the type of flower to be treated and the consistence or texture of the flower to be desirably obtained.

The colorants used in the present invention are of the type used in food industry, provided that they are soluble in the mixture and easily diffusible and fixable on the cellulosic tissue of the flower. Also, adequate colorants are those usually used in textile industry.

The mixtures used usually vary from a polymer percentage between 20% and 55% and an alcoholic solvent percentage from 45% to 80%.

Process time during this step goes from 12 to 72 h at room temperature, although it may be reduced from 2 to 12 h when operating with temperatures up to 100° C.

g) Evaporation (5)

After removing the mixture, the reactor (14) is subjected to vacuum during around 60 min, enough time to allow the evaporation of the majority of the solvent. Then, the vacuum is interrupted, the reactor (14) is opened and the supporting device (8) and the grids (7) are taken out along with the flowers using an elevated conveyor system.

The intracellular spaces of the flower are now filled with the mixture of polymers. Now, the flowers can be subjected, into the reactor, to a drying step using a hot air stream in order to completely evaporate the remaining solvent.

Drying may be made also by passing the supporting device (8) and the grids (7) along with flowers through a tunnel where hot air circulates.

It shall be understood that the above description is merely illustrative according to requirements of a sufficient disclosure and by no means limits the scope of the invention, which is defined only by the claims given below.

LIST OF REFERENCE SIGNS USED

1. Selecting and cutting
2. Assembling of the supporting device and grids
3. Dehydration
4. Infiltration
5. Evaporation
6. Packing
7. Grids
8. Supporting device
9. Central axle of supporting device
10. Channels of the grids
11. Spirals
12. Sharp tip
13. Tubular separators
14. Reactor
15. Feeder tank
16. Mix of solvents

The invention claimed is:

1. A method for preserving flowers, the method comprising:
   (a) preparing the flowers for preservation, the preparing the flowers for preservation comprising:
   selecting the flowers;
   cutting the flowers;
   immersing stems of the flowers in water;
   separating each of the stems from a remaining portion of each of the flowers, the remaining portions of each of the flowers comprising the non-stem portion of the flowers;
   assembling a supporting device, the supporting device comprising at least one grid, the assembling the supporting device comprising:
   placing each of the flowers in an opening of the at least one grid; and
   assembling the at least one grid on a central axle of the supporting device, wherein the at least one grid is placed at a distance along the central axle from an adjacent grid, the distance sufficient to prevent the flowers from being crushed by an adjacent grid and dependent on a height of the flowers;
   (b) implementing a first dehydrating step, the first dehydrating step comprising:
   filling the supporting device with flowers;
   placing the supporting device into a reactor;
   filling the reactor with a first mixture until the flowers are immersed in the first mixture, the first mixture comprising a water-miscible solvent and water, wherein the first mixture comprises more than 70% water-miscible solvent;
   maintaining the first mixture at a temperature between approximately room temperature and 100° C. for the time period, the time period comprising at least thirty minutes;
   extracting the first mixture from the reactor;
   (c) implementing a second dehydrating step, the second dehydrating step comprising:
   filling the reactor with a second mixture until the flowers are immersed in the second mixture, the second mixture comprising a water-miscible solvent and water, wherein the second mixture comprises more than 80% water-miscible solvent;
   maintaining the second mixture at a temperature between approximately room temperature and 100° C. for the time period;
   extracting the second mixture from the reactor;
   implementing a third dehydrating step, the third dehydrating step comprising:
   filling the reactor with a third mixture until the flowers are immersed in the third mixture, the third mixture comprising a water-miscible solvent and water, wherein the third mixture comprises more than 90% water-miscible solvent;
   maintaining the third mixture at a temperature between approximately room temperature and 100° C. for the time period;
   extracting the third mixture from the reactor;
   (d) optionally repeating the third dehydration step by progressively increasing the water-miscible solvent content in the mixture until virtually all water initially contained in the flowers has been replaced;
   (e) implementing an infiltration step, the infiltration step comprising:
   immersing the flowers in a bath mixture comprising
   a mixture of colorants;
   an infiltration mixture comprising a water-miscible infiltration solvent and water;
   a polymer soluble in the colorants and infiltration mixture; and, optionally,
   other substances aiding to give the flowers a desired color; and (f) implementing an evaporation step, the evaporation step comprising the bath mixture being removed from the flowers and the infiltration mixture being evaporated in a vacuum or by applying an evaporating temperature.

2. The method of claim 1, wherein in the flowers are at a desired opening point for obtaining a final open flowers product.

3. The method of claim 1, wherein the stems of the flowers are immersed into water for a period between approximately six to approximately 72 hours.

4. The method of claim 1, wherein in the stems of the flowers are cut at a distance from the non-stem portion, the distance between 1 centimeter and 2 centimeters for rose and carnation flowers, and between 10 centimeters to 15 centimeters for hydrangea flowers.

5. The method of claim 1, wherein in the flowers are placed in sharp tips of spirals of the grids.

6. The method of claim 5, wherein the grids are full of flowers.

7. The method of claim 1, wherein in tubular separators are placed between the grids.

8. The method of claim 1, wherein in the first mixture temperature is approximately 80° C.

9. The method of claim 1, wherein in the second mixture temperature is approximately 65° C.

10. The method of claim 1, wherein in the third mixture temperature is approximately 65° C.

11. The method of claim 1, wherein in the infiltration mixture temperature is approximately 65° C.

12. The method of claim 1, where in the water-miscible solvents of the first mixture, second mixture, third mixture, and infiltration mixture comprise an alcohol.

13. The method of claim 12, wherein the alcohol is ethanol.

14. The method of claim 1, wherein the bath mixture comprises between 20% and 55% polymers and from 45% to 80% alcoholic solvent.

15. The method of claim 1 or 14, wherein in the polymer is polyethylene glycol.

16. The method of claim 15, wherein a molecular weight of the polyethylene glycol is 400.

17. The method of claim 1, wherein the filling the reactor tank with the first mixture comprises:
passing the first mixture from a feeder tank to the reactor tank by introducing pressurized air into the feeder tank, and opening valves between the feeder tank and the reactor.

18. The method of claim 1, further comprising:
after extracting the first mixture, second mixture, third mixture, and infiltration mixture, recovering the mixtures using traditional methods.

19. The method of claim 1, wherein the temperature during the time period varies between room temperature and 100° C. according to the first mixture, second mixture, third mixture, and infiltration mixture temperatures, characteristics of the flowers.

20. The method of claim 1, wherein the infiltration step lasts for a period from 12 to 72 hours and wherein the bath mixture is at room temperature.

21. The method of claim 1, wherein the infiltration step lasts for a period from 2 to 12 hours and wherein the bath mixture is at a room temperature of up to 100° C.

22. The method of claim 1, wherein stainless steel cylindrical reactors are used under pressures up to 138 kPa, or under vacuum up to 77 kPa and temperatures up to 200° C.

23. The method of claim 1, where the grids of the supporting device comprise circular grids comprising a base, the base formed by metal channels allowing drainage of fluids from the grids, and wherein the metal channels comprise frustoconical stainless steel spirals having been welded wherein a bottom base wire is perpendicularly bent and ends in a sharpened tip wherein the flower stem is stuck.

24. The method of claim 23, wherein the grids are assembled on a central axle of the supporting device, wherein at least one grid is on top of an adjacent grid, and wherein the tubular separators are a size sufficient to prevent the flowers from being crushed by an adjacent grid and dependent on a height of the flowers, the size dependent on the height of the flowers.

25. The method of claim 18, wherein the traditional methods comprise distillation.

* * * * *